United States Patent [19]

Sucholeiki

[11] Patent Number: 5,779,985

[45] Date of Patent: Jul. 14, 1998

[54] REACTION PLENUM

[75] Inventor: Irving Sucholeiki, Watertown, Mass.

[73] Assignee: Solid Phase Sciences Corporation, Watertown, Mass.

[21] Appl. No.: 762,887

[22] Filed: Dec. 7, 1996

Related U.S. Application Data

[60] Provisional application No. 60/008,742, Dec. 18, 1995.

[51] Int. Cl.$^6$ .................................................. B06B 1/00
[52] U.S. Cl. .......................... 422/128; 422/63; 422/65; 435/287.3; 436/177; 436/809
[58] Field of Search ............................ 422/128, 116, 422/131, 65, 63; 436/177, 808, 809; 435/286.1, 287.3

[56] References Cited

U.S. PATENT DOCUMENTS

| | | |
|---|---|---|
| 3,552,536 | 1/1971 | Emary. |
| 3,811,623 | 5/1974 | Speer. |
| 3,837,805 | 9/1974 | Boucher ................................ 422/128 |
| 3,951,605 | 4/1976 | Natelson ................................ 422/65 |
| 4,022,579 | 5/1977 | Revillet et al. ......................... 422/65 |
| 4,259,290 | 3/1981 | Souvaniemi et al. .................. 422/65 |
| 4,582,990 | 4/1986 | Stevens ................................. 422/65 |
| 4,638,032 | 1/1987 | Benner ................................ 525/54.11 |
| 4,919,807 | 4/1990 | Morton ................................ 210/388 |
| 5,320,944 | 6/1994 | Okada et al. ........................ 435/7.94 |
| 5,380,487 | 1/1995 | Choperena et al. .................. 422/63 |
| 5,446,263 | 8/1995 | Eigen et al. ......................... 219/521 |
| 5,496,517 | 3/1996 | Pfost et al. ............................ 422/63 |

FOREIGN PATENT DOCUMENTS

| | | |
|---|---|---|
| 211 436 | 2/1987 | European Pat. Off.. |
| WO 83/03920 | 11/1983 | WIPO. |
| WO 93/25912 | 12/1993 | WIPO. |

OTHER PUBLICATIONS

Fjeld, J.G., et al.:*J. Immunol. Methods*, vol. 109, p. 1, 1988.

Miltenyi, S. et al.:*Cytometry*, vol. 11, p. 231, 1990.

Padmanabhan, R., et al.:*Analytical Biochem*, vol. 170, p. 341, 1988.

Treleaven, J.G., et al.; *Lancet*, vol. 14, p. 70, 1984.

*Primary Examiner*—Hien Tran
*Attorney, Agent, or Firm*—Jerry Cohen; Jacob N. Erlich

[57] ABSTRACT

An apparatus for facilitating the running of multiple simultaneous solid phase reactions for mounting on a temperature controllable water bath and a method of using this apparatus in the presence or absence of paramagnetic beads to perform chemical syntheses resulting in separation and recovery of a final desired reaction product is provided. The apparatus comprises a reaction plate, a reaction vessel for mounting in the reaction plate, a reaction plate holder, a screw-like rod, a mounting block attached to the reaction plate holder for operably receiving the screw-like rod, a motor, a sonication region in the water bath and a magnetic separation region in the water bath. Paramagnetic beads having reaction sites are introduced into the reaction vessels along with the appropriate solvent and one or more reactants. The contents of the reaction vessel are sonicated, then moved to the magnetic separation region where the paramagnetic beads are tightly held against the reaction vessel while the solvent is aspirated off. Once the desired reaction product is attained, the reaction product is cleaved off the paramagnetic bead. In an alternative embodiment, chemical synthesis is performed in a similar manner in the absence of the paramagnetic beads.

13 Claims, 7 Drawing Sheets

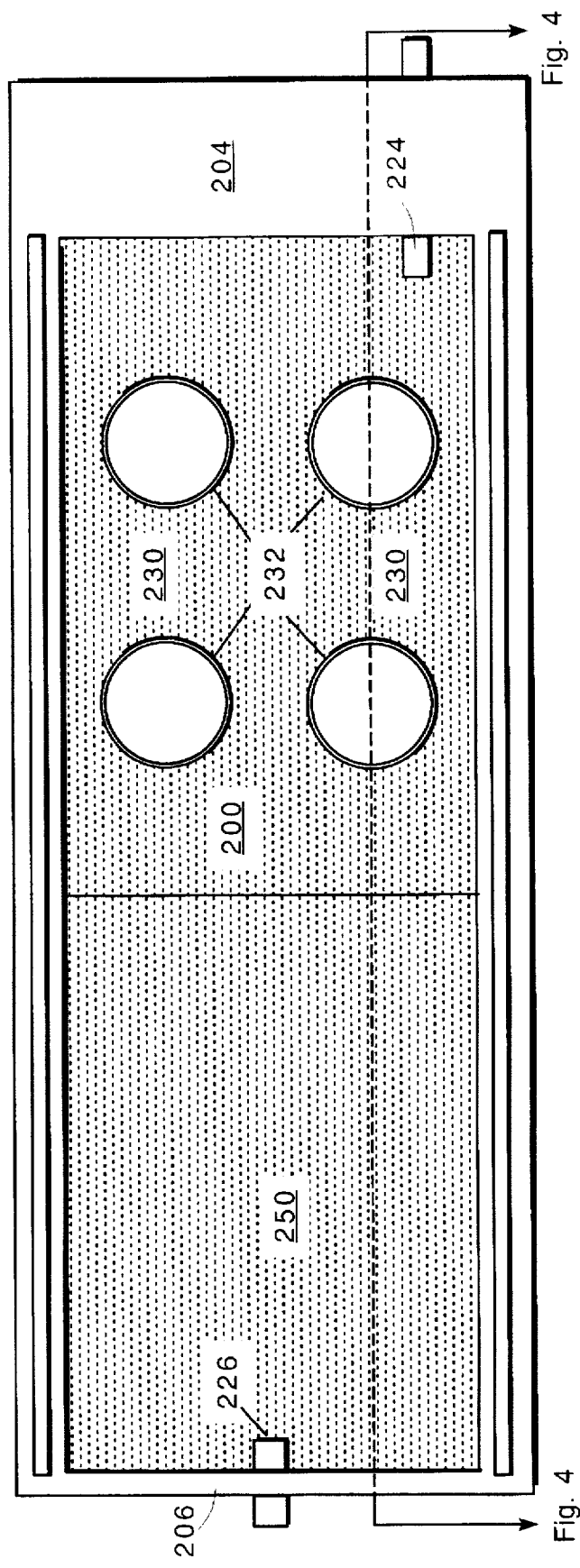

REACTION PLENUM

CROSS REFERENCE TO RELATED APPLICATION

This application claims the benefit of U.S. Provisional Application Ser. No. 60/008.742, filed Dec. 18, 1995.

FIELD OF THE INVENTION

The present invention relates to an apparatus and a method for using that apparatus for separation of magnetic particles in solution. Further, the inventive apparatus provides for selective recovery of desired chemical reaction products, especially where the desired chemical reactions involve organic solvents. The apparatus and method find use in the field of solid phase organic synthesis.

BACKGROUND OF THE INVENTION

In the field of solid-supported organic synthesis the physical separation of the support from the solubilized components of the reaction mixture has primarily been accomplished by filtration through a glass or polymer filter. Although filtration has been the method of choice in both solid-phase peptide and nucleotide synthesis it does have limitations that warrant the development of new approaches. One such limitation is the difficulty in automating the simultaneous washing and filtration of hundreds of small scale solid-phase reactions. A field that has had some success in translating some of its techniques into automation is immunodiagnostics. Exposing antibody-bound paramagnetic beads to a magnetic field can be used to separate antibody-bound antigen from unbound antigen in immunoassays.[1,2] Magnetic separation methods have also been applied successfully in cell sorting.[3-5] A definite advantage that magnetic separation has over simple filtration is the ability to separate out particles in small reaction volumes. The use of magnetic separation in the field of solid-supported organic chemistry has been slow in coming due to the instability exhibited by the currently available supports in organic solvents such as dimethylformamide and methylene chloride. Upon exposure to these solvents the typical polymer coated magnetic beads dissolve. Silica coated magnetic beads as well as high cross-linked polystyrene paramagnetic beads have become available which are more stable to these solvents and can withstand higher temperatures.[6]

Equipment to mechanically separate out paramagnetic particles or beads is known.[7,8] Unfortunately, these apparati and methods are primarily aimed at solid phase biochemical reactions which are normally run at room temperature and in buffered water. The development of equipment to heat, agitate and magnetically separate paramagnetic particles in one integrated machine would be instrumental in facilitating the use of paramagnetic particles in solid-phase organic synthesis. Further, a means for enhancing the rate of reaction during organic synthesis to increase the efficiency is desirable.

OBJECTIVES

It is therefore an object of this invention to provide an apparatus, termed a reaction plenum, which can facilitate the running of multiple simultaneous solid phase reactions using high energy, variable amplitude sonication.

Another object of this invention is to provide an apparatus (reaction plenum) which can effectively mix and separate paramagnetic particles in a multiple array format.

Lastly, the object of this invention is to integrate the use of high energy, variable amplitude sonication and magnetic separation into one system.

SUMMARY OF THE INVENTION

The inventive apparatus comprises a reaction plate with wells sized to receive one or more reaction vessels. A reaction plate holder is provided to support the reaction plate or plates essentially at the water level of a water bath that is capable of providing a temperature controlled environment. A first mounting block or a number of first mounting blocks depending upon the size of the reaction plate holder is seated on the reaction plate holder. The first mounting block has a hole sized to receive a supporting rod which preferably is threaded to make the rod screw-like. The supporting rod is rotatably attached to a motor, preferably by a connector. Preferably, the hole in the first mounting block is threaded, so that when the motor is activated, the supporting rod rotates causing the first mounting block by virtue of the threaded interior of the hole to move linearly above the water level of the bath. A second mounting block is attached to the reaction plate holder and is not threaded so that it acts primarily to guide the screw-like rod.

In a first embodiment of the instant invention, the water bath is provided with a sonication region at its proximal end and a magnetic separation region at its distal end. An inlet tube is provided at the proximal end of the water bath and an outlet tube is provided at the distal end of the water bath to allow free circulation of water through the bath. Paramagnetic beads having reaction sites are dispensed into the reaction vessels. Generally, the motor, the rod, the reaction plate, the reaction vessel, the first and second mounting blocks, the reaction plate holder, the sonication region and the magnetic separation region are collectively termed a reaction plenum.

In a second embodiment of the instant invention, the paramagnetic beads are absent. Generally, only the sonication region is present.

To use the first embodiment, the reactants in solvent are added to the reaction vessel. The contents of the reaction vessel are sonicated. The motor is activated thus advancing the reaction plate holder with the reaction plate(s) and reaction vessel(s) towards the magnetic separation region. The magnetic separation is activated causing the paramagnetic beads to be retained in the reaction vessel. The solvent and remaining reactants are aspirated from the reaction vessel, leaving the reaction product attached to the paramagnetic bead. The reaction product is then cleaved from the paramagnetic bead. If desired, the paramagnetic bead may be washed where appropriate. Further, the steps of addition of reactant(s), sonication, and magnetic separation can be repeated until the desired reaction product is attained. Then, the reaction product is cleaved from the paramagnetic bead. The reactants added at each step are dependent upon the desired reaction product structure desired.

When chemical synthesis is performed in the absence of the paramagnetic beads, magnetic separation is unnecessary. Separation of reaction product from reactants may be achieved by a number of known means such as chromatography or electrophoresis.

BRIEF DESCRIPTION OF THE DRAWINGS

FIG. 5 illustrates a top down view of the water bath bottom.

DETAILED DESCRIPTION OF THE PREFERRED EMBODIMENTS

The reaction plenum provided by the present invention which has been made to attain the objectives mentioned above comprises a water bath, four 96-well reaction plates, a plate holder which mechanically slides along a longitudinal plane which is substantially parallel to the surface of the water in the water bath, a screw and motor assembly which facilitates the movement of the plate holder and a water bath which is segregated into two differentiated regions that emit ultrasonic waves or a magnetic field.

The reaction plenum functions to mix the magnetic beads in a organic synthesis reaction mixture using variable amplitude ultrasonic waves produced through a series of commercially available sonicating cup horns embedded in a region comprising half of the water bath. The sonicating cup horns are also intended to enhance the reaction rate of solid phase organic chemical reactions by transferring energy from the horns, through the glass reaction vessels on to the surface, and into the cavities of the paramagnetic beads also termed a paramagnetic support. Magnetic separation of the paramagnetic support is accomplished with a permanent magnetic field produced through a series of commercially available neodymium magnetic discs embedded in the region of the water bath at the end opposite the sonicating cups. Upon activation of the motor and screw assembly, the plate holder carrying the four 96-well plates is caused to slide from the sonicating region where the sonication cups are located to the magnetic separating region where the neodymium magnetic disc arrays are located in the water bath.

The solid phase chemical reactions for which the reaction plenum can be used include general organic chemical reactions such as acetylations, alkylations, saponifications, metal mediated Stille couplings, Suzuki reactions, Mitsunobu reactions and reductive aminations. When low energy sonication is used the reaction plenum can also be used to assist in the mixing and separation of solid phase biological assay reactions such as immunological, enzymatic and agglutination reactions. The embodiment described will provide dimensions and reaction volumes for use in a small molecule drug discovery application. But the invention is not to be construed as particularly restricted to any of the cited examples or dimensions should the apparatus be used for larger scale organic synthesis. Modifications pertaining to other applications would be apparent to one skilled in the art.

The present invention will be described referring to the accompanying drawings.

Figure 1A:
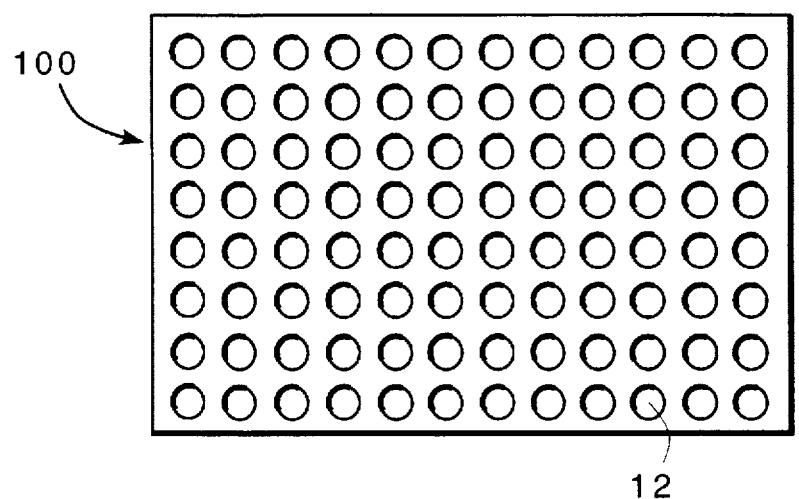
FIG. 1A represents a top view of a schematic representation of a 96-vessel reaction plate.

The reaction plate (generally referenced in all drawings as 100) which is seen in top view in FIG. 1A is made of a organic solvent stable material such as polypropylene. Its dimensions are approximately 3¼ inches by 4¹⁵⁄₁₆ inches for this application. Each reaction plate has a well (12) sized to retain a reaction vessel (14). The reaction plate (100) shown in FIG. 1A has 96 wells drilled therein. Each well has a reaction vessel which is a glass or Pyrex reaction vessel (14) which is a tube, 1½–3 inches long and ⅛–⅜ inches wide, seated therein. The reaction vessel tubes are inserted in such a manner that their bottoms pass through the reaction plate wells and extend at least ¼ inch or more into the water bath (generally referenced as 200 in subsequent drawings) at its closed end.

Figure 1B:
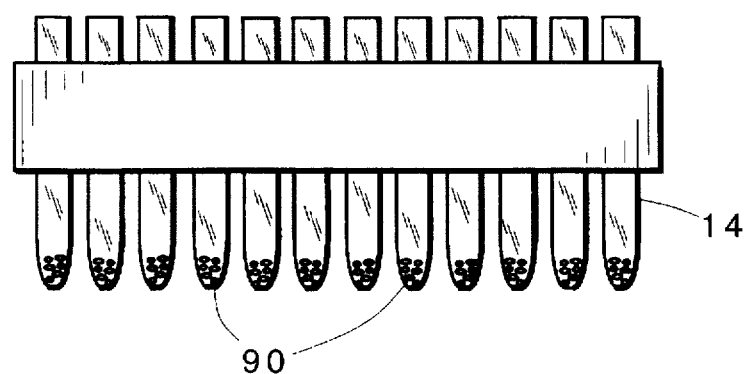
FIG. 1B represents a side view of a schematic representation of the 96-vessel reaction plate of FIG. 1A which illustrates the positioning of reaction vessels in the reaction plate.

FIG. 1B illustrates a series of reaction vessels each containing one or more paramagnetic beads (90). A plurality of paramagnetic beads is preferred. The paramagnetic beads to be placed in each reaction vessel may include polystyrene based paramagnetic beads, silica based paramagnetic beads and others. Paramagnetic beads that can be used with the instant invention include, for example, those described U.S. Pat. Nos. 4,554,088 (Whitehead, et al.) which discloses paramagnetic particles comprising a metal oxide core surrounded by a coat of polymeric silane; U.S. Pat. No. 5,356,713 (Charmot), which discloses a magnetizable microsphere comprised of a core of magnetizable particles surrounded by a shell of a hydrophobic vinylaromatic monomer; U.S. Pat. No. 5,395,688 (Wang) which discloses a polymer core which has been coated with a mixed paramagnetic metal oxide-polymer layer, the disclosure of each incorporated herein by reference. Also useful is another paramagnetic bead which utilizes a polymer core to adsorb metal oxide such as for example in U.S. Pat. No. 4,774,265 (Ugelstad), incorporated herein by reference. Paramagnetic beads having a plurality of primary beads or particles, each of which is a polymer coated or polymer encapsulated metal oxide which has inducible magnetic properties encapsulated in a mesh or matrix comprised of a thermoplastic polymer resin such as disclosed in Sucholeiki, et al. (U.S. Provisional Patent Applic. No. 60/003,233) may also be used. Preferably, the paramagnetic beads have a reaction site attached there to or can be treated to provide a reaction site. Useful reaction sites for the instant application include a plurality of aminomethyl sites or a plurality of Rink linker sites. Other useful paramagnetic beads with reaction sites or that can be caused to posses reaction sites would be known to those skilled in the art.

Figure 2A:
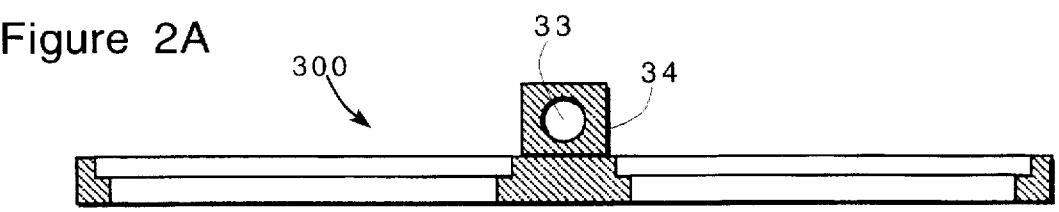
FIG. 2A represents a cross-sectional side view of a reaction plate holder at a mounting block.
Figure 2B:
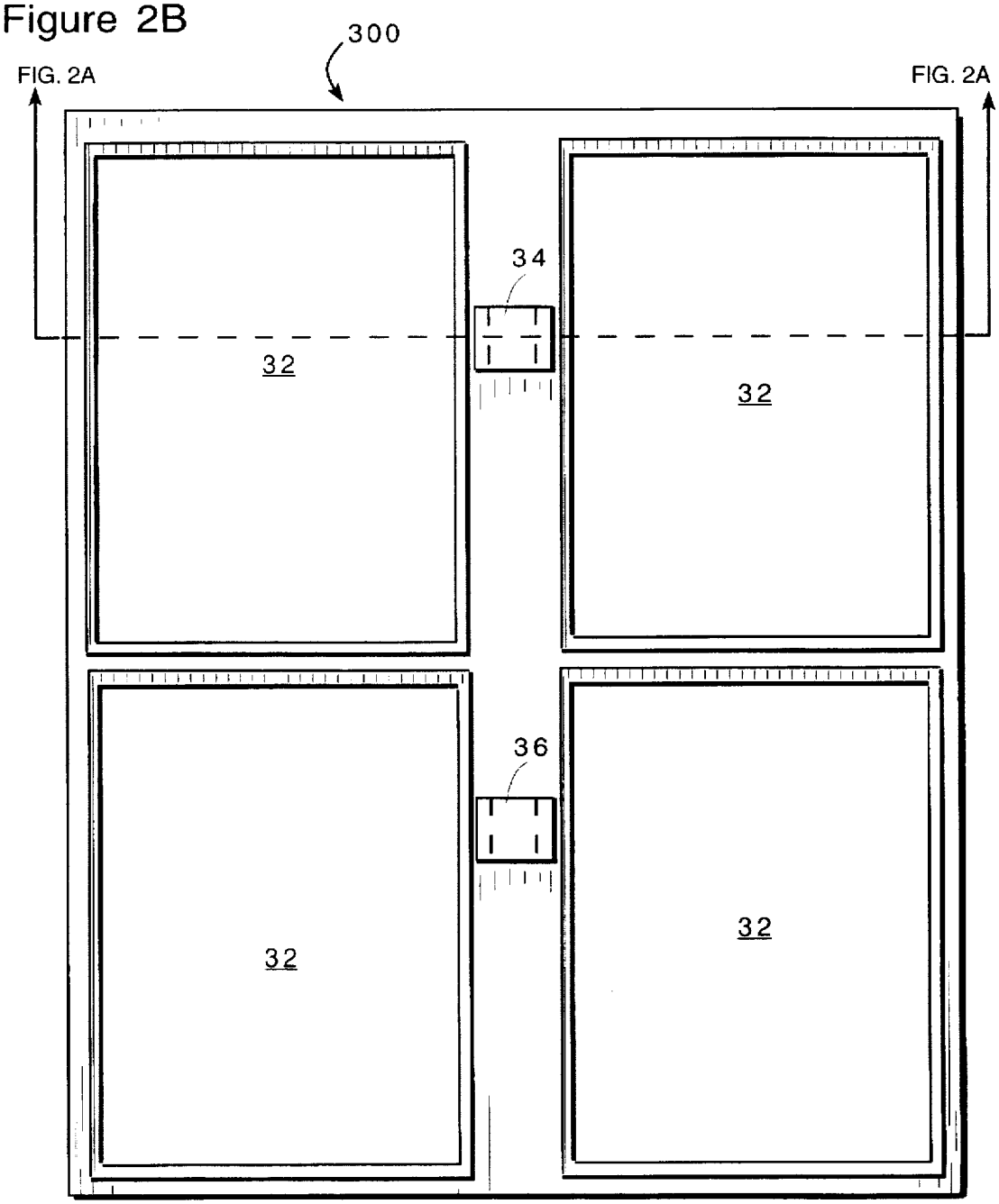
FIG. 2B represents a top view of a plate holder for four reaction plates.

FIG. 2A is a graphical representation showing a side cross-sectional view of the mounting block region of the reaction plate holder. FIG. 2B is a top view of the reaction plate holder (generally referenced in all drawings as 300). The reaction plate holder (300) is about 12 inches in width and 23 inches in length for this application. It is made of ¼ inch thick acrylic. The plate holder (300) can accommodate up to four 96-well reaction plates. Each reaction plate (100) is inserted into one hole (32) of the four square cut holes shown in the plate holder (300). In FIG. 2A, seated and firmly attached at the top of the plate holder is a first square mounting block (34). FIG. 2B illustrates the placement of a first (34) and a second mounting block (36). Each mounting block is placed between two square cut holes (32). Each mounting block is approximately a ½ inch cube made of Delrin, an acetal (DuPont; Wilmington, Del).

The first mounting block (34) is provided with a threaded hole (33) having approximately 13 threads/inch. The second block (36) contains a non-threaded ½ inch diameter hole. The second block (36) is used primarily to guide the screw (generally referenced as 40 in subsequent drawings). The first block (34) acts as a screw nut.

Figure 3A:
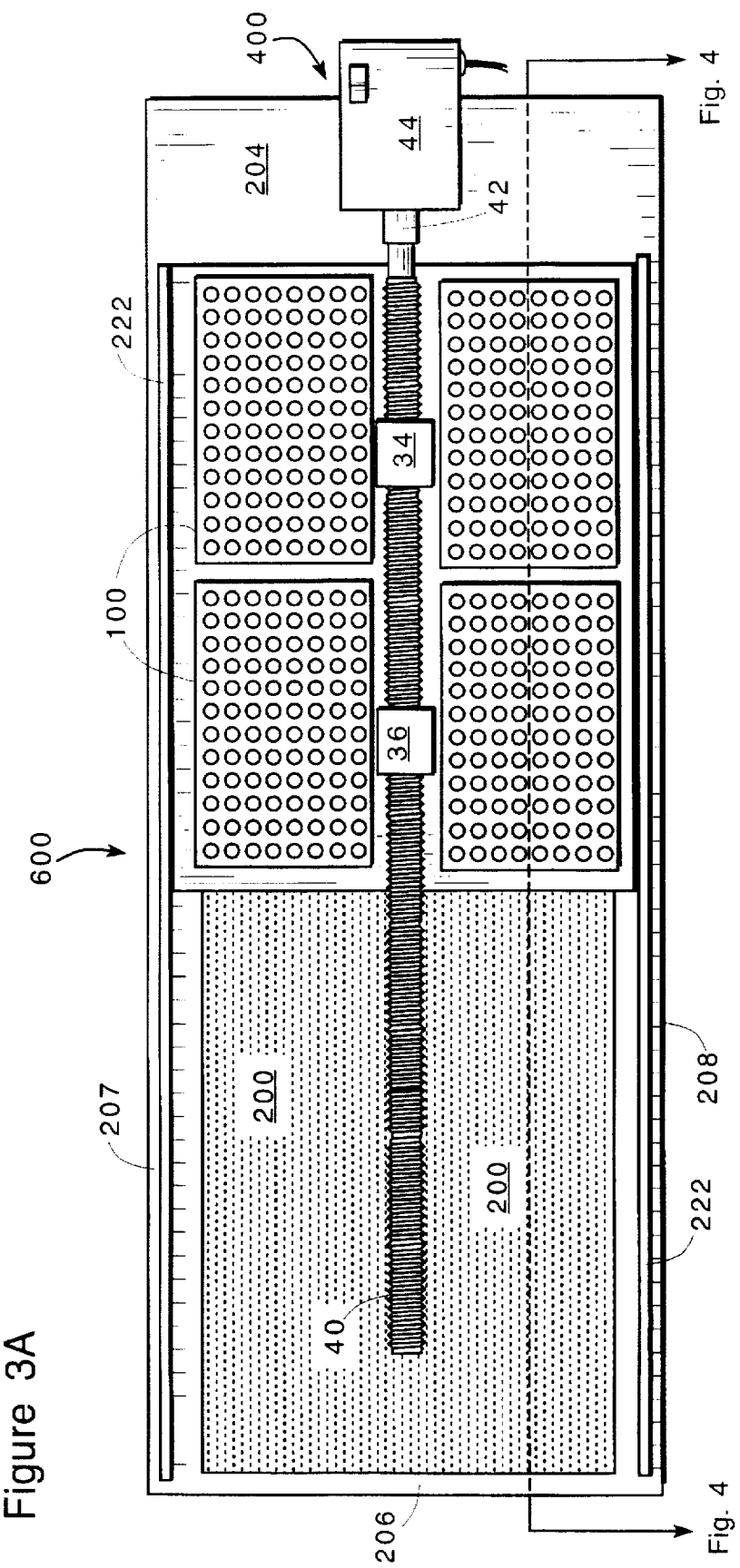
FIG. 3A represents a schematic top view of a reaction plenum having a plate holder having four reaction plates and a motor driven screw seated over a water bath.
Figure 3B:
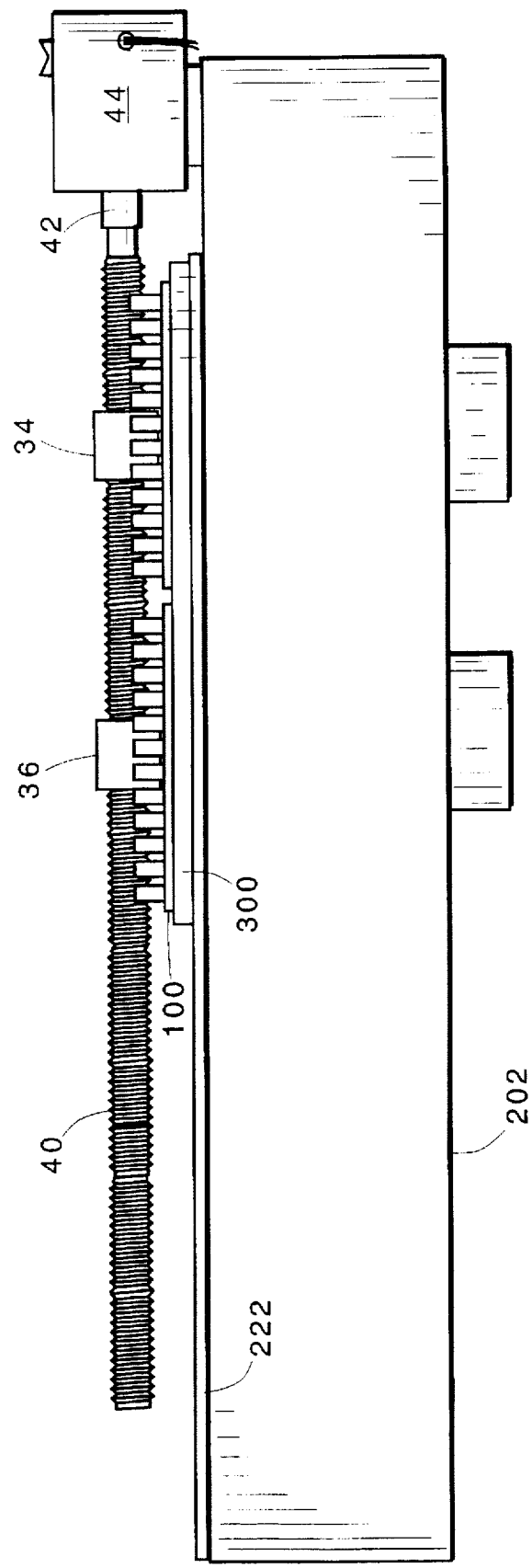
FIG. 3B represents a schematic side view of the reaction plenum of FIG. 3A.

The complete apparatus (600) termed a reaction plenum is illustrated in FIG. 3A in top view and in FIG. 3B in side view. The reaction plenum (600) is comprised of four 96-well reaction plates (100), the reaction plate holder (300), a screw (40), and a motor assembly (generally referenced as 400). The water bath (200) is essentially an open box having a bottom (202), a thickened proximal end (204) for supporting a motor, a thinner distal end (206), and two side walls (207 and 208 respectively). Each side wall has a slide guard (222) positioned along its length. The screw (40) is approximately 26 inches long and approximately ¼ to ½ inch in diameter with approximately 13 threads/inch. The screw (40) is attached to a metal coupling (42)(5/16 inch ID). The coupling (42) is attached to a Clifton Precision 30 Volt DC motor (44). The motor (44) is powered by a 100–240 volt AC 60 cycles power supply with a AC Adapter and a 13.5 volt DC (2.0 amp) output. Upon activating the motor (44) clockwise or counter-clockwise, the screw (40) is made to turn which causes the reaction plate holder (300) to slide back and forth depending on the direction of the rotation of the screw (40).

Figure 4:
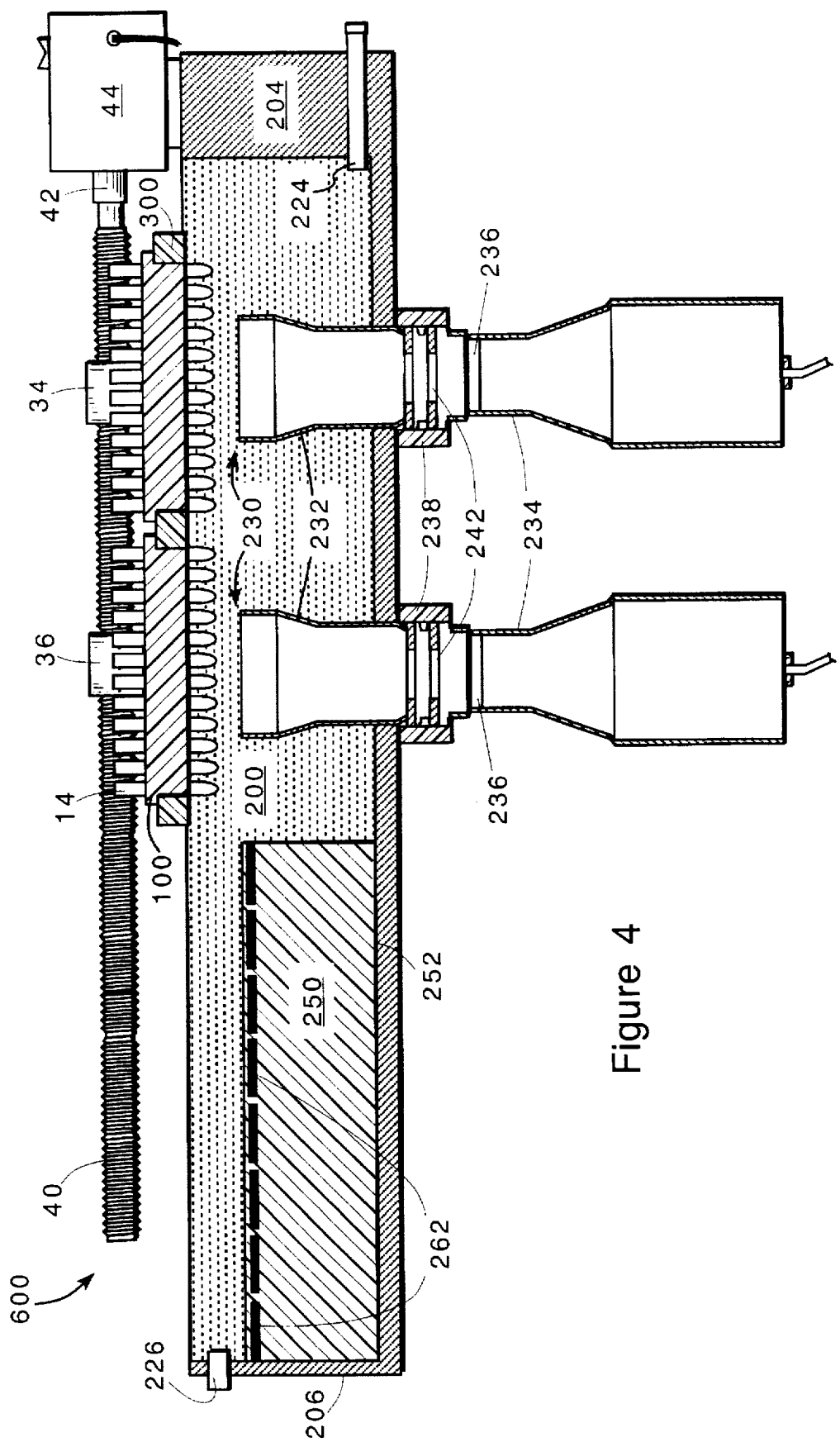
FIG. 4 represents a cross-sectional side view of the reaction plenum of FIG. 3A.

FIG. 4 illustrates a cross sectional side view of the reaction plenum (600). The water bath distal wall, side walls and bottom are made of approximately ¼ inch thick acrylic panels, all of which are bolted together with the thicken proximal end to form the open box. Each seam is waterproofed using sealant. The water bath may also be solvent sealed and/or vacuum drawn. The water bath (200) has inserted at its proximal end an inlet port (224) and at its distal end, an outlet port (226) to allow the free flow of water. The sonication region (230) of the water bath is composed of about one to four commercially available Misonix's brand (Farmingdale, N.Y.) sonicating cup horns. Each cup horn (232) has a radiating face diameter of 2.5 inches (550 watts) and protrudes through the bottom of the water bath (200). To each sonicating cup horn (232) is attached a separate 20 KHz converter or transducer (234) which is held in place using clamps (236). Each sonicating cup horn protrudes through an approximately ¼ inch thick acrylic tube (238) containing two 3 inch-in-diameter o-rings (242). The acrylic tubes are sealed to the bottom of the water bath (200). The magnetic separation region (generally referenced as 250) is composed of an acrylic box (252) which is approximately 11 inches in length, 8.5 inches in width and 2.5 inches deep. The acrylic box (252) is fixedly attached to the bottom of the water bath (200). Embedded in and spread out along the entire top of the box are arrays of commercially available approximately ½ inch diameter neodymium magnetic discs (262) (Master Magnetics, Inc; Castle Rock, Colo.). As shown, the motor (44) is positioned proximal to one end of the water bath, outside the interior of the water bath (200) itself. The screw (40) extends substantially parallel to the surface of the bottom (202) of the water bath (200) from the motor (44) towards the opposite end of the water bath (200). The screw (40) supports and positions the reaction plate holder (300) above the water bath (200) at about the water level between the slide guards (222).

FIG. 5 illustrates a top down view of the water bath (200) indicating the positioning of the four Misonix's brand sonicating cup horns (232) in the sonicating region (230) at the water bath bottom. An inlet port (224) is shown protruding through the proximal wall (204) adjacent to the sonicating region (230). An outlet port (226) is shown positioned in the distal end (206) of the water bath proximal to the magnetic separation region (250).

Figure 6B:
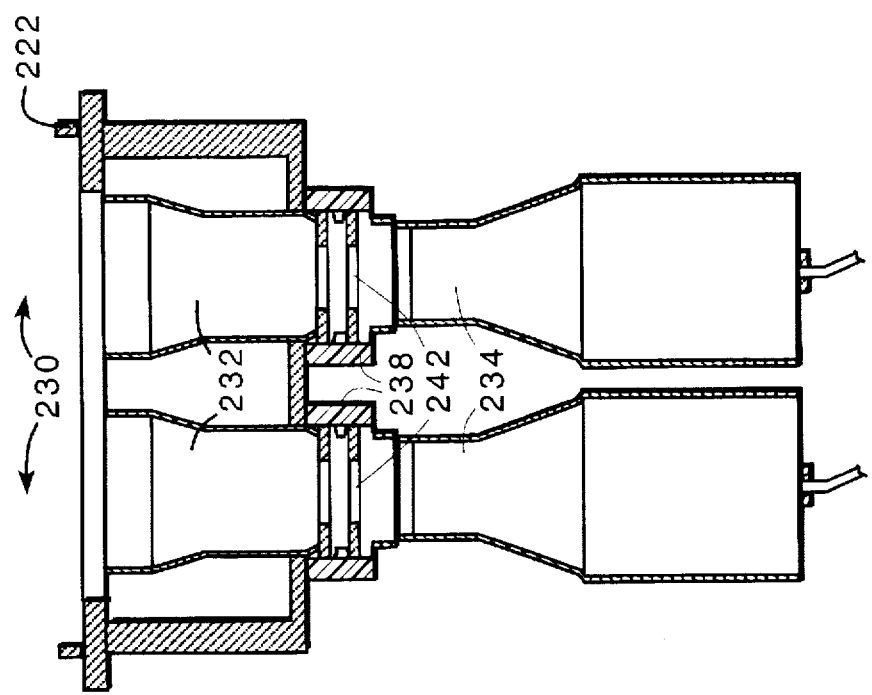
FIG. 6B illustrates a cross-sectional end view of the sonication region of the reaction plenum.
Figure 6A:
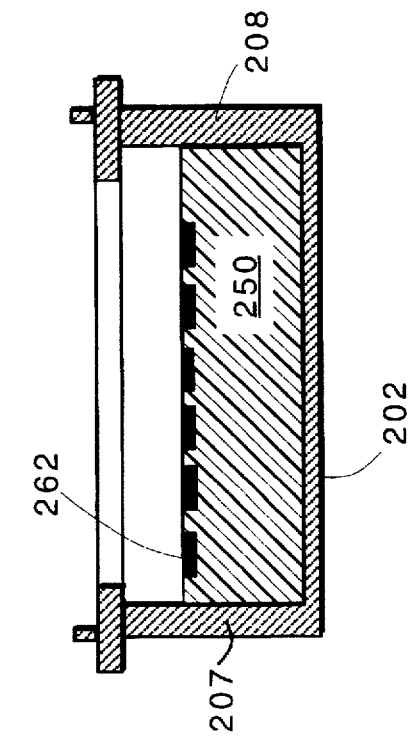
FIG. 6A illustrates a cross-sectional end view of the magnetic separation region of the reaction plenum.

FIG. 6A illustrates a cross-sectional of the end of the water bath at the magnetic separation region of the reaction plenum and the positioning of the neodymium magnetic discs (262) in the magnetic separation region relative to the side walls of the water bath. Slide guards (222) are shown positioned at the top end of the water bath walls and are separated one from the other by about 8.5 inches. In contrast, the walls of the bath are about 9.5 inches one from the other. The width of the water bath including the slide guards is about 15 inches. FIG. 6B illustrates a cross-sectional view of the sonication region including the sonicating cups (232), the o-rings (242), the acrylic rings for mounting the cups (238), and the converter (234). Also illustrated is the positioning of the components of the sonication region relative to the water bath walls as viewed at the end of the water bath opposite the magnetic separation region.

The variable amplitude, ultrasonic waves produced by the sonicating cup horns travel through the water and through the glass reaction vessels and to the paramagnetic beads within resulting in an enhancement of the reaction rate of a solid phase reaction and/or assisting in the mixing of the reaction mixture. This process can occur only when the reaction plate holder is positioned over the sonicating region of the bath. Upon activation of the motor, the plate holder moves longitudinally on to the area of the bath containing the neodymium magnetic arrays. Once positioned over these arrays, the magnetic particles become attracted to the bottom of the reaction vessels. This allows for the manual or automated removal of the solvent and the soluble components of the reaction mixture through suction. Upon reversing the rotation of the motor the reaction plate holder can again longitudinally slide back over the sonication region of the water bath. The reaction plate and reaction plate holder may repeatedly slide back and forth between the sonication region and the magnetic separation region depending on the task to be performed. The reaction block may be used manually or can be automated. The preferred embodiment has the reaction block integrated with a commercially available x-y-z automated solvent delivery robot.

In order to further specify the process of this invention, the following examples are provided. It will be recognized by those skilled in the art that these examples represent only specific implementations of the process of the invention. They in no way limit its scope.

Alternatively, chemical synthesis reactions can be performed as subsequently described but in the absence of paramagnetic beads. Sonication will faciliate production of the desired reaction product and reactants can be separated from reaction products by known means such as chromatographically or by electrophoresis.

EXAMPLE 1

Stepwise Synthesis of Glycyl-Alanyl Linker on Magnetic Composite Particles (Scheme 1).

a) Coupling and Deprotection of Linker.

To one of the reaction vessels mounted in the reaction vessel plate seated in the reaction plate holder is added 25 mg (0.017 mmole) of aminomethyl magnetic composite particles (obtained from Polymer Laboratories, Church Stretton, UK). Using a commercially available two arm X-Y-Z Tecan 5052 Liquid Handling Robot (Research Triangle Park, N.C.) a solution of 50 microliters (11.4 mmole) of diisopropylethylamine dissolved in 1.5 mL of methylene chloride is added by robotic needle syringe. The mixture is then sonicated using the Misonix's brand (Farmingdale, N.Y.) sonicating cup horns for 1 minute. After 1 minute the reaction vessel is mechanically transferred to the magnetic separation region and after another 1 minute interval, the liquid in the reaction vessel is aspirated using the Tecan liquid handling robot. To the reaction vessel is then added 2-3 ml of methylene chloride. The mixture is then sonicated on low power for 30 seconds. The reaction vessel is then mechanically moved to the magnetic separation region and the solvent removed by aspiration. This process is then repeated two more times. To the reaction vessel containing is then added (using the Tecan Liquid Handling Robot) 42.5 mg (0.078 mmole) of p-[(R,S)-a-[1-9H-fluoren-9-yl)-methoxbenzyl]-phenoxyacetic acid (Fmoc) linker dissolved in 1.5 mL of dimethylformamide and then 12.5 microliters (0.079 mmole) of diisopropylcarbodiimide dissolved in 1.5 mL of anhydrous methylene chloride in that order.

b) Synthesis of Gly-Ala bound to Rink amide linker.

In this Example, a-N-Fmoc-substituted amino acids are abbreviated Fmoc-Xxx, where Xxx is the conventional three-letter abbreviation for any of the amino acids. To the Fmoc protected magnetic particles of the previous example is added 0.4 mL of 50 % piperidine in dimethylformamide and mixture sonicated on low power following the protocol 20 seconds "on" and 40 seconds "off" over a period of 20 minutes. The reaction vessel is then transferred to the magnetic separation region and the soluble components of the reaction mixture removed by aspiration using the Tecan robot. To the reaction vessel is then added 3 ml of dimethylformamide and the mixture is sonicated on low power for 30 seconds. The reaction vessel is then moved to the

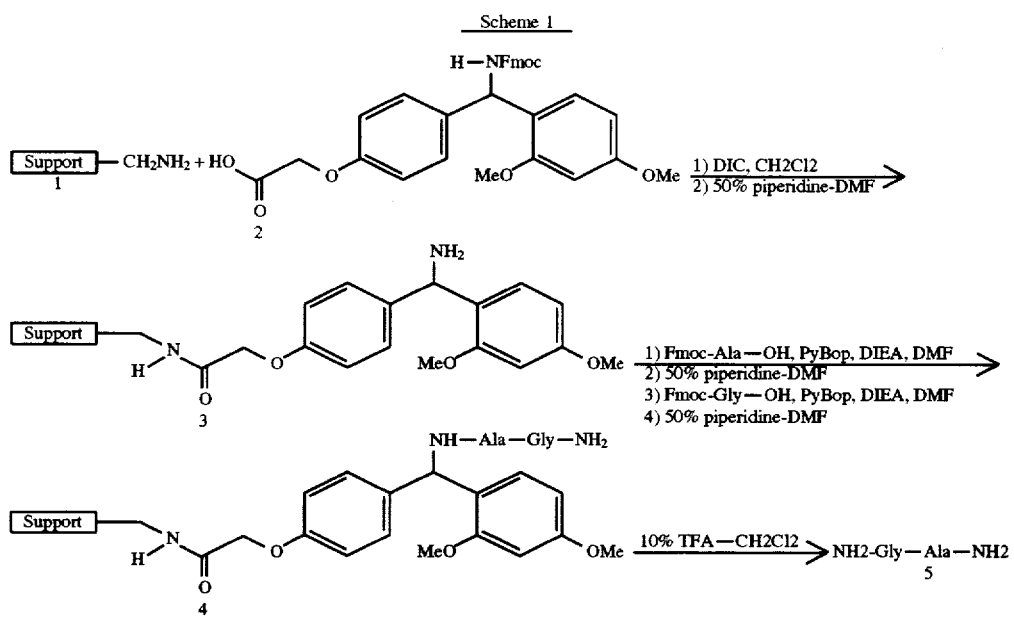

The mixture is then sonicated on low energy following the program of 20 seconds "on" and 40 seconds "off" over a period of 8 hours. The reaction vessel is then mechanically transferred to the magnetic separation region and the soluble components of the reaction mixture are removed by aspiration using the Tecan robot. To the reaction vessel is then added 2-3 ml of methylene chloride and the mixture is sonicated on low power for 30 seconds. The reaction vessel is then mechanically moved to the magnetic separation region and the solvent is removed by aspiration. This process is then repeated three more times. To the particles is then added 50 microliters (0.285 mmole) of DIRA dissolved in 1 mL of methylene chloride and 25 microliters (0.26 mmole) of acetic anhydride dissolved in 0.5 ml of methylene chloride and the mixture sonicated on low power following the protocol 20 seconds "on" and 40 seconds "off" over a period of 2 hours. The reaction vessel is then transferred to the magnetic separation region and the soluble components of the reaction mixture removed by aspiration using one of the liquid robotic arms. To the reaction vessel is then added 2 ml of methylene chloride and the mixture is sonicated on low power for 20 seconds. The reaction vessel is then moved to the magnetic separation region and the solvent is removed by aspiration. This process is then repeated two more times and then the paramagnetic beads are washed with 2 ml of methanol using the same protocol a total of two times. Finally, the paramagnetic beads bearing the reaction product are washed with methylene chloride a total of three times in that order.

magnetic separation region and the solvent is removed by aspiration. This process is then repeated three more times, then washed with 2 ml of methanol using the same protocol a total of two times, and then finally washed with methylene chloride a total of three times in that order.

To the deprotected particles is added a solution of 32 mg (0.1 mmoles) of a-N-Fmoc-Ala in 0.5 mL of DMF, 50 mg (0.1 mmole) of benzotriazole-1-yl-oxy-tris-pyrrolidinophosphoniumhexafluorophosphate (PyBop) in 0.5 mL of DMF and 40 microliters (0.23 mmole) of diisopropylethylamine in 1 mL of DMF and the mixture sonicated on low power following the protocol 20 seconds "on" and 40 seconds "off" over a period of 2 hours. The reaction vessel is then mechanically transferred to the magnetic separation region and the soluble components of the reaction mixture removed by aspiration using the Tecan robot. To the reaction vessel is then added 3 ml of dimethylformamide and sonicated on low power for 30 seconds. The reaction vessel is then moved to the magnetic separation region and the solvent removed by aspiration. This process is then repeated three more times, then washed with 2 ml of methanol using the same protocol a total of two times, and then finally washed with 2 ml methylene chloride a total of three times in that order. To the reaction vessel is then added 0.4 mL of 50% piperidine in dimethylformamide and the mixture is sonicated on low power following the protocol 20 seconds "on" and 40 seconds "off" over a period of 20 minutes. The reaction vessel is then transferred to the magnetic separation region and the soluble components of the reaction mixture are removed by aspiration using the Tecan robot. To the reaction vessel is then added 3 ml of dimethylformamide and the mixture is sonicated on low power for 30 seconds. The reaction vessel is then moved to the magnetic separation region and the solvent removed by aspiration. This process is then repeated three more times, then washed with 2 ml of methanol using the same protocol a total of two times, and then finally washed with methylene chloride a total of three times in that order. Coupling and deprotection of Fmoc-Gly was accomplished in the same manner as just described for the first Fmoc-Ala reaction to give, after piperidine deprotection, resin bound Gly-Ala-linker magnetic composite particles.

Additional amino acids can be added as desired following the above procedure.

EXAMPLE 2

Cleavage of Gly-Ala Off Magnetic Composite Particles (Scheme 1).

To dried resin is added 2 mL of a 10% trifluoroacetic acid (TFA) in methylene chloride and the mixture is sonicated on low power following the protocol 20 seconds "on" and 40 seconds "off" for a total of 20 minutes. The paramagnetic particles are then magnetically separated and the liquid is siphoned off using one of the robot arms of the Tecan. To the paramagnetic particles is added another 2 mL of 10% TFA-$CH_2Cl_2$ solution and the mixture is sonicated on low power following the protocol 20 seconds "on" and 40 seconds "off" for a total of 20 minutes. The paramagnetic particles are again magnetically separated. The liquid is siphoned off and combined with the previous acid wash. The volatile components are removed under reduced pressure to give an oil. The oil is precipitated from diethyl ether to give the dipeptide as the trifluoroacetic acid salt.

Modifications and variations can be made to the disclosed embodiments without departing from the subject and spirit of the invention as defined in the following claims. Such modifications and variations, as included within the scope of these claims, are meant to be considered part of the invention as described.

REFERENCES

1) Ugelstad, J.; Ellingsen, T.; Berge, A.; Helgee, B.; 1983, PCT Int. Appl. W083/03920.
2) Fjeld, J. G.; Benestad, H. B.; Stigbrand, T.; Nustad, K. J. *Immunol. Methods* 1988, 109, 1.
3) Treleaven, J. G.; Gibson, J.; Ugelstad, J.; Rembaum, A.; Philip, T.; Caine, G. C.; Kemshead, J.; *Lancet*, 1984, 14, 70.
4) Miltenyi, S.; Muller, W.; Weichel, W.; Radbruch, A. *Cytometry*, 1990, 11, 231.
5) Padmanabhan, R.; Corsico, C. D.; Howard, T. H.; Holter, W.; Fordis, C. M.; Willingham, M.; Bruce, H. *Analytical Biochem.*, 1988, 170, 341.
6) Benner, S. A. 1987, U.S. Pat. No. 4,638,032
7) Higo, Y.; 1986, PCT European App. EP 86110787.
8) Hawkins, T.; Sulston, J.; Watson, A. 1993, PCT Int. Appl. W093/25912.

What is claimed is:

1. An apparatus for performing a chemical synthesis reaction on a paramagnetic bead, said apparatus comprising:

a means for sonication mounted in a water bath at a first end of said water bath;

a means for magnetic separation mounted in said water bath at a second end of said water bath;

a motor located proximate said water bath;

a glass reaction vessel for containing the paramagnetic bead;

a reaction plate located in said water bath and having a well sized to receive said glass reaction vessel such that at least a portion of said glass reaction vessel is located below a water level of said water bath;

a rod connected to said motor; and a means for rotatably mounting said reaction plate to said rod whereby activation of said motor results in rotation of said rod thereby moving said reaction plate between said means for sonication and said means for magnetic separation.

2.) The apparatus of claim 1 wherein said means for rotatably mounting said reaction plate comprises a reaction plate holder.

3. The apparatus of claim 1 wherein said means for sonication is a transducer.

4.) The apparatus of claim 3 wherein said means for magnetic separation is a magnetic disc.

5.) The apparatus of claim 4 wherein said magnetic disc is comprised of neodymium.

6.) The apparatus of claim 5 wherein said rod is threaded.

7. The apparatus of claim 6 wherein said means for rotatably mounting said reaction plate comprises a reaction plate holder, a first mounting block seated on said reaction plate holder and a second mounting block seated on said reaction plate holder.

8.) The apparatus of claim 7 wherein said first mounting block has a threaded hole sized to receive said rod and said second mounting block has a non-threaded hole sized to receive said rod.

9.) The apparatus of claim 1 further comprising a means for circulating water in said water bath.

10.) The apparatus of claim 9 wherein said means for circulating said water comprises an inlet at said first end of said water bath and an outlet at said second end of said water bath.

11. An apparatus for separating a reactant from a solvent, said apparatus comprising:

a glass reaction vessel for containing said reactant, said solvent, and at least one paramagnetic bead;

a means for sonication of said solvent and said paramagnetic bead mounted proximate to a bottom of a water bath;

a means for magnetic separation of said at least one paramagnetic bead from said solvent mounted proximate to said bottom of said water bath; and a means located in said water bath for positioning at least a portion of said glass reaction vessel below a water level in said water bath.

12. The apparatus of claim 11 further comprising a means operably connected to said glass reaction vessel for transporting said glass reaction vessel between said means for sonication and said means for magnetic separation.

13. The apparatus of claim 11 further comprising a means for providing a temperature controlled environment in said bath.

* * * * *